United States Patent [19]

Foà et al.

[11] Patent Number: 5,326,801
[45] Date of Patent: Jul. 5, 1994

[54] POLYMER COMPOSITIONS CONTAINING ORGANIC PHOSPHITE STABILIZERS

[75] Inventors: Marco Foà; Sauro Strologo, both of Novara, Italy

[73] Assignee: Himont Incorporated, Wilmington, Del.

[21] Appl. No.: 921,952

[22] Filed: Jul. 28, 1992

Related U.S. Application Data

[62] Division of Ser. No. 794,552, Nov. 19, 1991, Pat. No. 5,162,548.

[30] Foreign Application Priority Data

Nov. 20, 1990 [IT] Italy ................. 22118 A/90

[51] Int. Cl.$^5$ ............ C08K 5/527; C08K 5/529; C07F 9/6574
[52] U.S. Cl. .................... 524/109; 524/111; 524/119; 549/218; 558/78
[58] Field of Search ................ 524/119, 109

[56] References Cited

U.S. PATENT DOCUMENTS 4,673,701  6/1987  Minagawa et al. .............. 524/99

Primary Examiner—Robert W. Ramsuer
Assistant Examiner—Michael G. Ambrose

[57] ABSTRACT

New organic phosphites of a specific formula are used as stabilizers for polymers and other organic materials.

3 Claims, No Drawings

POLYMER COMPOSITIONS CONTAINING ORGANIC PHOSPHITE STABILIZERS

This application is a division of application Ser. No. 07/794,552, filed Nov. 19, 1991, now U.S. Pat No. 5,162,548.

The invention relates to a new class of organic phosphites capable of acting as stabilizers for organic materials, for example polymers, and the polymer compositions comprising them.

It is well known that polymers substances, such as polyolefins, tend to rapidly degrade upon exposure to air or oxidizing agents in general and light. Said degradation, which brings about a break down of their physical characteristics, is increased by the various heat treatments to which polymers are subjected during manufacturing.

Stabilizers are used in the practice in order to counteract said degradation. None of them by itself shows adequate properties for complete protection of the polymer from oxidizing agents, light and heat treatments, therefore, the polymer industry uses mixtures of stabilizers which present specific actions (for example antioxidants, U.V. stabilizers, U.V. radiation absorbers). Usually, in these mixtures one finds an organic oxygenated phosphorus compound, in particular a phosphite or an organic phosphonite. The specific action of the above phosphorus compounds can be summarized as follows:

1) they counteract the alteration of the molecular weight of the polymer which takes place during the processing of the polymer;
2) they reduce the coloration (e.g. yellowing) of the polymer following heat treatments;
3) they act as secondary antioxidant by preventing the formation of free radical phenomena which cause degradation.

Some classes of organic phosphites and phosphonites are widely used in the polymer stabilization field.

In particular, a compound representative of phosphites used as stabilizers is the tris(2,4-di-tert-butyl-phenyl)phosphite.

A phosphonite widely used is the tetrakis (2,4-di-tert-butyl-phenyl)4,4'-diphenylenediphosphonite.

Other organic phosphites used in the polymer stabilization filed are described, for example, in U.S. Pat. No. 4,673,701.

The present invention provides a new class of organic phosphites capable of giving results particularly advantageous in the polymer stabilization field compared to the other stabilizers known up to now.

Said class of organic phosphites is represented by formula

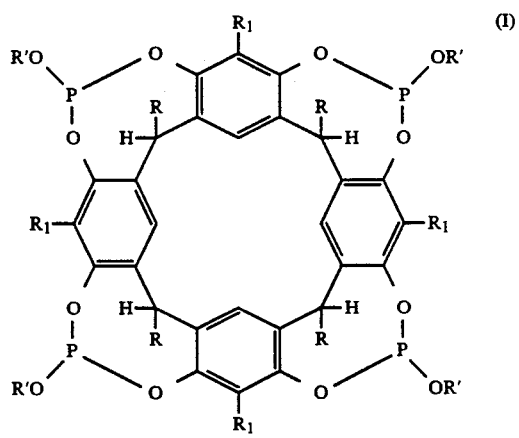

where R, same or different, are H or linear or branched $C_1$–$C_{30}$ alkyl radicals, $C_5$–$C_6$ alicyclic radicals; $C_7$–$C_{12}$ aralkyl radicals; heteroaromatic or aromatic radicals, optionally substituted in the para and/or meta positions, by one or more electron donor groups such as, for example, the alkyl and alkoxyl groups; R', same or different, are $C_1$–$C_{30}$ alkyl radicals, or $C_5$–$C_{30}$ simple or condensed alicyclic radicals; $C_6$–$C_{30}$ aryl radicals, simple double or condenced, optionally substitued, preferably with $C_1$–$C_9$ alkyl groups, or with $C_6$–$C_{10}$ aryl groups Joined by a heteroatom (in particular O, S, NH), or by a $C(R_2R_3)$ group, where $R_2$ and $R_3$, same or different, are H, $C_1$–$C_5$ alkyl or $C_6$–$C_{10}$ aryl radicals; $R_1$, same or different, are H or $C_1$–$C_4$ alkyl radicals; with the proviso that when R is H, $R_1$ are $C_1$–$C_4$ alkyls.

Preferably, the R radicals are selected from the group consisting of: H, methyl, ethyl, propyl, isopropyl, n-butyl, isobutyl, tert-butyl, n-pentyl, n-hexyl, n-heptyl, n-octyl, n-nonyl, n-decyl, n-undecyl, benzyl, 2-phenylethyl, phenyl, tolyl, para-ethylphenyl, paramethoxyphenyl, p-tert-butylphenyl, 2-furfuryl, 2-cyclohexylethyl and p-phenylphenyl.

Preferably the R' radicals are selected from the group consisting of: $C_{20}H_{35}$(tetrahydroabietyl), $C_{18}H_{37}$(stearyl), 2-t-butyl-4-methyl-phenyl, 2-t-butyl-4-propyl-phenyl, 2-tert-butyl-4-isopropylphenyl, 2-tert-butyl-4-n-butylphenyl, 2-tert-butyl-4-isobutyl-phenyl, 2-tert-buytl-4-tert-butyl-phenyl, 2-tert-butyl-4-tert-octyl-phenyl, 2-tert-butyl-4-tert-nonyl-phenyl, 2,6-di-tert-butyl phenyl, 2,6-di-tert-butyl-4-methyl-phenyl, 2,6-di-tert-butyl-4-ethyl-phenyl, 2,6-di-tert-butyl-4-propyl-phenyl, 2,6-di-tert-butyl-4-propyl-phenyl, 2,6-di-tert-butyl-4-isopropyl-phenyl, 2,6-di-tert-butyl-4-n-butylphenyl, 2,6-di-tert-butyl-4-sec-butylphenyl, 2,6-di-tert-butyl-4-tert-butylphenyl, 2,6-di-tert-butyl-4-tert-octylphenyl and 2,6-di-tert-butyl-4-tert-nonylphenyl.

Examples of phosphites of the formula (1) are those where the R radicals are the same and selected from the group consisting of: methyl, ethyl, propyl, n-butyl, iso-butyl, n-pentyl, benzyl, 2-phenyl-ethyl, phenyl, para-ethylphenyl, paramethoxy-phenyl, p-tert-butylphenyl and p-phenylphenyl; the R' radicals are the same and selected from: $C_{20}H_{35}$(tetrahydroabietyl), 2,4-di-tert-butylphenyl and 2,4,6-tri-tert-butylphenyl; and the R' radicals are the same and selected from H and methyl.

The phosphites of formula (1) can be prepared starting from the compounds of formula (2)

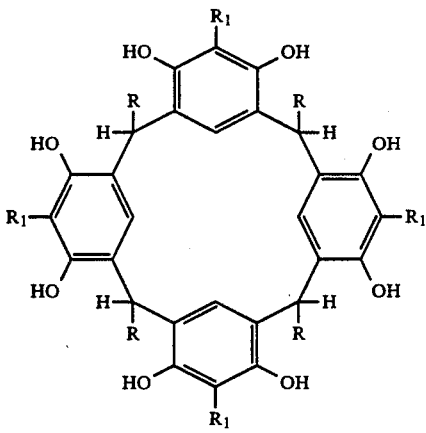

(2)

where R and $R_1$ have the meaning indicated above for the phosphites of formula (1), by way of the synthesis exemplified by the following equation:

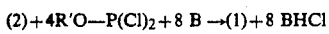

(2) + 4 R'O—P(Cl)$_2$ + 8 B → (1) + 8 BHCl where R' has the meaning indicated above for the phosphites of formula (1).

The reaction is carried out preferably in the presence of an acid acceptor represented by the compound B. Both organic and inorganic compounds may be used as acid acceptors; the preferred ones are the tertiary amines, such as for example the triethylamine, pyridine bases and ammonia.

Preferably the reaction is carried out in a solvent medium. Preferred solvents are aromatic hydrocarbons (for example benzene, toluene and xylene); chlorinated organic compounds, such as chloroform and dichloroethane; ethers, such as, for example, ethyl ether, diglyme and tetraglyme; and dipolar aprotic solvents, such as, for example, dimethylformamide.

The reaction temperature is generally from ambient temperature to that of the boiling point of the solvent used.

The phosphites of formula (1) are isolated using the usual separation and purification techniques for organic compounds, such as for example filtration to separate the phosphite (1) from the B HCl adduct, and evaporation of the solvent, and, optionally, crystallization or distillation.

Formula (2) compounds can be obtained according to the reaction shown below (analogous to the one described in the Journal of American Chemical Society, 1940 (62) page 2512):

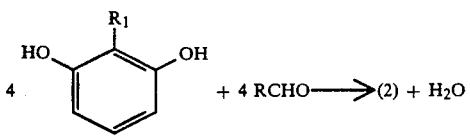

Said reaction is carried out in an acid environment. Examples of this reaction are found in the Journal of American Chemical Society, 1980 (102) page 6046, Journal of Organic Chemistry, 1980 (45) page 4498, Journal of Organic Chemistry, 1988 (53) page 5475 and Journal of Organic Chemistry, 1989 (54) page 1305.

Compounds of the R'O—PCl$_2$ type can be prepared according to the following reaction:

R'OH + PCl$_3$ + B' → R'O—PCl$_2$ + B'HCl where R' has the meaning indicated above for the phosphites of formula (1), B' is an acid acceptor which is the same or different from compound B and is preferably selected from the ones preferred for compound B set forth above. This reaction is preferably carried out in a solvent medium. The preferred solvents are aromatic hydrocarbons (for example benzene, toluene, and xylenes); chlorinated compounds such as chloroform and dichloroethane; ethers such as for example ethyl ether, diglyme and tetraglyme; and dipolaf aprotic solvents, such as dimethylformamide. Said solvent can be equal or different from the one used for the synthesis of the phosphites of formula (1).

Whenever the solvent is the same, the compounds of the R'O—PCl$_2$ type can be used in the subsequent preparation without being isolated. If the solvent is different, they are isolated after the B'HCl adducts have been separated by evaporation of the solvent and can be used without further purification.

The phosphites of the present invention are capable of stabilizing polymers which are sensitive to thermal and oxidizing degradation, as well as other organic substances, such as mineral or synthetic fluids (lubricating oils for example).

Small quantities of the phosphites, which are the object of this invention, are used to provide the stabilization. The suitable quantity of phosphites that can be used in order to obtain the stabilizing effect is generally from 0.01 to 3 parts by weight per 100 parts by weight of the material to be stabilized.

Particularly, the present invention also includes polymer compositions comprising the phosphites of formula (1) in a quantity from 0.01 to 3 parts by weight per 100 parts of the polymer material to be stabilized.

The polymers for which the phosphites of formula (1) have shown to be particularly effective as stabilizers include:

Polymers and copolymers, or their mixtures obtained by way of sequential polymerization of R''—CH=CH$_2$ olefins, where R'' is a hydrogen atom or a C$_1$-C$_6$ alkyl radical, or aryl radical, preferably phenyl. In particular, said polymers and copolymers comprise:

1) isotactic or mostly isotactic polypropylene;
2) HDPE, LLDPE and LDPE polyethylene;
3) crystalline copolymers of propylene with ethylene or other α-olefins, or both such as for example 1-butene, 1-hexene, 1-octene and 4-methyl-1-pentene;
4) elastomeric ethylene/α-olefin copolymers, and ethylene/α-olefin/diene terpolymers containing minor proportions of diene, where the α-olefin is preferably selected from propylene, 1-butene, 1-pentene, 1-hexene, 4-methyl-1-pentene, 3-methyl-1-butene (examples of dienes which are most commonly present in the above mentioned elastomeric copolymers are butadiene, ethylidene-norbornene and 1,4-hexadiene);
5) heterophasic polymers obtained by way of sequential polymerization, consisting of (A) a homopolymer propylene fraction, or one of the copolymers of (3), and (B) a copolymer fraction formed of (4).

Other examples of polymers for which the organic phosphites of formula (1) have shown to be effective as stabilizers are the following: Polymers of di-olefins or cycloolefins, such as for example polyisoprene, polybutadiene, polycyclopentene, polynorbornene and their mixtures, or their copolymers or terpolymers.

Copolymers of mono and diolefins with other vinyl comohomers, such as for example ethylene-alkylmethacrylates and ethylene-vinyl acetates.

Polystyrene or polymethylstyrene, and copolymers of styrene or methylstyrene with other dienes or acrylic derivatives, such as for example styrene-butadiene and styrene-acrylonitrile copolymers, and corresponding terpolymers, such as for example styrene-butadiene-methylacrylate terpolymers; mixtures of copolymers of styrene and other polymers, such as for example polyacrylates; block polymers containing styrene, such as for example styrene-ethylene-propylene-styrene or styrene-butadiene-styrene.

Polymers obtained by grafting the styrene, by itself, or in combination with another acrylic monomer, on unsaturated polymers, such as for example styrene grafted on polybutadiene, or styrene and alkylacrylates grafted on polybutadiene or styrene and acrylonitrile grafted on ethylene-propylene-diene terpolymers, and mixtures of these polymers with the ones described above.

Polymers containing halogen atoms, such as for example polychloroprene and chlorinated rubber, or homopolymers and copolymers of epichlorohydrin, or polyvinylidene fluoride, or copolymers of halogenated monomers, such as for example vinyl chloride-vinyl acetate copolymers.

Polymers obtained from $\alpha$-$\beta$ unsaturated acids or their derivatives, such as for example polyacrylates, or polyacrylamides, or polyacrylonitrile; their copolymers with the monomers listed above, such as for example acrylonitrile-butadiene or acrylonitrile-vinyl halide copolymers.

Polymers obtained from amines and unsaturated alcohols or their acyl or acetal derivatives, such as for example polyvinyl acetate or maleate.

Homopolymers of copolymers obtained from cyclic ethers such as for example polyethylene oxide.

Polyacetals such as poyoxymethylene and copolymers with ethylene oxide.

Polyphenylene oxide and its mixtures with polystyrene.

Polyurethanes, polyamides and copolyamides, such as for example, 6/6 or 6/10 polyamide and their copolymers with polyethers.

Polyureas, polyimides and polyamides-imides.

Polyesters, such as for example polyethylene terephthalate, and polycarbonates.

Polyether ketones, polyether sulfones, polysulfones.

Cross-linked polymers, such as for example phenol-formaldehyde, or melamine-formaldehyde resins, or unsaturated polyesters with a vinyl compound as crosslink agent.

Acrylic thermosetting resins, such as the ones derived from epoxyacrylates.

Any mixture of the polymers mentioned above.

Natural polymers, such as rubber, or cellulose and chemically modified cellulose materials.

Other organic materials to which the phosphites of formula (1) can be added to favor stabilization to oxidation are: mineral, vegetable or animal oils, and their mixtures, for example with paraffin wax, or mixtures of synthetic esters with mineral oils, such as those used as plastifiers for polymers; aqueous emulsions of synthetic or natural rubbers.

The stabilizers of the present invention can be easily incorporated into the polymers by way of conventional techniques at any stage of production preceding the formation of the manufactured article. The stabilizer can be mixed with the polymer by way of various techniques, such as dry mixing in the form of powder, or wet mixing in the form of solutions, suspensions, or even in "masterbach". In said operations the polymer can be used in the form of powder, pellets, solutions, suspensions or latexes.

The phosphites of the present invention can be added in conjunction with other conventional polymer additives, such as for example antioxidants, U.V. absorbers, Ni-based stabilizers, pigments, reinforcing agents, plasticizers, antiacids, antistatic agents, flame retardants, lubricants, corrosion inhibitors, metal complexing agents, and nucleating agents.

For example, commonly used antioxidants are: 2,6-dialkylphenols, derivatives of alkylated hydroquinones, hydroxylated thiodiphenyl ethers, alkylidene hisphenols, O-, N- and S- benzyl compounds, hydroxybenzyl malonates, hydroxybenzyl aromatic compounds, s-triazine compounds, amides of $\beta$-(3,5-di-tert-butyl-4-hydroxyphenyl)propionic acid, esters of $\beta$-(3,5-di- tert-butyl-4-hydroxyphenyl)propionic acid with alcohols containing one or more hydroxyl groups, esters of 3,5-di-tert-butyl-4-hydroxyphenyl acetic acid with alcohols containing one or more hydroxylic groups, benzyl phosphonates.

Examples of light stabilizers commonly used are: benzoic acid esters, optionally substituted, hindered amine light stabilizers (HALS) and oxalic acid diamides.

Other additives which may by present in the compositions stabilized are this esters, such as for example dilauryl thiodioprionate.

An example of preferred composition according to the invention comprises 100 parts by weight of polymer to be stabilized (preferably a polyolefin) and:

A) from 0.05 to 5 parts by weight of a phenolic antioxidant, and

B) from 0.01 to 3 parts by weight of one of the phosphites of the invention.

The following examples are given in order to illustrate and not limit the present invention. All the percentages indicated are by weight.

In the examples reported below the organic phosphites of the invention are characterized by way of mass spectroscopy, D.C.I. (direct current ionization) method, to determine the molecular weight, and by way of infrared rays (I.R.) spectroscopy. In particular, for each one of the phosphites prepared according to Examples 1–6, the existence of absorption bands in the 1010–1080 $cm^{-1}$ and 810–830 $cm^{-1}$ ranges, which are characteristics of aliphatic P-OC and aromatic P-OC respectively, is confirmed by I.R.

The compounds of formula (2), which according to Examples 1–6 are used to prepare the organic phosphites of the invention, are prepared in the following manner.

Preparation of 1, 8, 15, 22, tetraundecyl [1$_4$] metacyclophane 3, 5, 10, 12, 17, 19, 24, 26, octol.

Into a 250 ml flask equipped with a magnetic agitator, thermometer, refrigerator and gas inflow tube, are introduced under argon atmosphere 19.8 g (0.18 moles) of resorcinol and 75 ml of ethanol at 95%. To this solution are added 25 ml of concentrated hydrochloric acid. The mixture is cooled to 2° C., and 33.2 g (0.18 moles) of dodecanal in 50 ml of ethanol are added slowly a period of 2 hours. The solution is slowly heated to 25° C., and then brought to 75° C. for 21 hours. The precipitate that is formed is separated and washed with cold methanol. The solid is crystallized from the methanol obtaining 34.2 g of the desired product (68% yield).

The product is recognized from an elementary analysis: C%=78.01 (theoretical 78.21); H%=10.31 (theoretical 10.21).

The structure has been confirmed by mass spectrum and N.M.R. spectrum analyses.

The octols are prepared in a similar way starting from

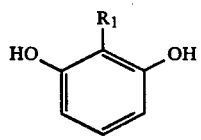

compounds, and RCHO, where R and $R_1$ have the meanings defined above for the phosphites of formula (1).

EXAMPLE 1

Preparation of 1,8,15,22-tetraundecyl [1$_4$]metacyclophane-3-26,5-10; 12-17,19-24, tetra-tetrahydroabietyl phosphite (Compound N.1).

Into a 100 ml flask equipped with an agitator are introduced, under nitrogen atmosphere, 1.1 g (1 millimole) of 1,8,15,22-tetraundecyl [1$_4$] metacyclophane 3, 5, 10, 12, 17, 19, 24, 26, octol, 1.57 g of tetrahydroabietyl dichlorophosphite (4 millimoles), and 0.81 g of triethylamine (8 millimoles) in 50 ml of toluene. The mixture is heated in reflux for 24 hours. Then the ammonium salt that is formed is filtered, and the solid is washed with toluene. The toluene solutions are gathered and evaporated under vacuum separating 2.1 g of desired product (88% yield). The product obtained has the following elementary analysis: C%=75.95 (theoretical 76.4); H%=10.5 (theoretical 10.3); P%=4.55 (theoretical 5.2); molecular weight $(MH)^+ = 2385$ [where $(MH)^+$ = molecular Weight of the substance plus protone].

EXAMPLE 2

Preparation of 1,8,15,22-tetraundecyl [1$_4$]metacyclophane-3-6,5-10,12-17,19-24, tetrakis(2,4-di-tert-butylphenyl)phosphite (Compound N. 2).

In the same type of apparatus and with same method used in Example 1, substituting the abietyl dichlorophosphite (4 millimoles) with 1.22 g (4 millimoles) of 2,4-di-tert-butyl dichlorophosphite, one obtains 1.9 g (93% yield) of the desired product. The product obtained has the following elementary analysis: C%=74.8 (theoretical 75.25); H%=9.09 (theoretical 9.27); P%=5.9 (theoretical 6.06); molecular weight $(MH)^+ = 2041$.

EXAMPLE 3

Preparation of 1,8,15,22-tetraundecyl [1$_4$]metacyclophane-3-26,5-10,12-17,19-24 ,tetrakis(2,4,6-tert-butylphenyl)phosphite (Compound N. 3).

Into a 250 ml flask using the same method as Example 1, are introduced 2 g (1.82 mmoles) of 1,8,15,22-tetraundecyl[1$_4$] metacyclophane-3, 5, 10, 12, 17, 19, 24, 26-octol, 2.65 g of 2,4,6-tri-tert-butylphenyl dichlorophosphite, and 1.47 g of triethylamine in 100 ml of toluene. Using the procedure of Example 1 are isolated 3.7 g (90% yield) of desired product. The product obtained has the following elementary analysis: C%=75.8 (theoretical 76.28); H%=9.51 (theoretical 9.78); P%=5.1 (theoretical 5.47); molecular weight $(MH)^+=2265$.

EXAMPLE 4

Preparation of 1,8,15,22-tetramethyl [1$_4$]metacyclophane-3-26,5-10,12-17,19-24, tetra-tetrahydroabietyl phosphite (Compound N. 4)

Into the same apparatus of Example 3 are introduced 1.5 g (1.75 mmoles) of 1,8,15,22-tetramethyl [1$_4$]metacyclophane-3, 5, 10, 12, 17, 19, 24, 26-octol, 1.5 g of tetrohydroabietyl dichlorophosphite, and 1.5 g of triethylamine, in 100 ml of toluene.

Using the same method of Example 1,2.5 g (50% yield) of desired product are isolated.

The product obained has the following elementary analysis: C% =73.41 (theoretical 73.67); H%=9.27 (theoretical 9.05); P%=6.60 (theoretical 6.77); molecular weight $(MH)^+=1824$.

EXAMPLE 5

Preparation of 1,8,15,22-tetraphenyl [1$_4$] metacyclophane-3-26,5-10,12-17,19-24, tetra-tetrahydroabietyl phosphite (Compound N. 5)

Into the same apparatus of Example 1 are introduced 1.7 g (2.14 moles) of 1,8,15,22-tetraphenyl [1$_4$] metacyclophane 3, 5, 10, 12, 17, 19, 24, 26-octol, 100 ml of dimethylformamide, and 2.4 ml of triethylamine and 3.3 g of tetrahydroabietyl dichlorophosphite are added. After 3 hours at 50° C. the solvent is evaporated under vacuum, then 100 ml of toluene are added, and the product is filtered and the solid washed with 50 ml of toluene are added, and the product is filtered and the solid washed with 50 ml of toluene. The toluene extracts are evaporated, thus obtaining 3.9 g (88% yield) of the desired product.

The product obained has the following elementary analysis: C%=76.0 (theoretical 76.42); H%=8.1 (theoretical 8.36); P%=5.72 (theoretical 5.97); molecular weight $(MH)^+=2075$.

EXAMPLE 6

Preparation of 4,11,18,25-tetramethyl [1$_4$]metacyclophane-3-26,5-10,12-17,19-24, tetra-tetrahydroabietyl phosphite (Compound N. 6)

Into the same apparatus of Example 3 are introduced 1.62 g of 4,11,18,25-tetramethyl [1$_4$]methocyclophane 3, 5, 10, 12, 17, 19, 24, 26-octol (3 mmoles) dissolved in a mixture of 10 ml of dimethylformamide and 50 ml of toluene. To the solution are added 3.3 ml of triethylamine (24 Moles) and then 50 ml of a toluene solution of 4.7 g consisting of tetrohydroabietyl dichlorophosphite.

The mixture is maintained under agitation for 12 hours at 60° C. The solid, after having been separated, is filtered and washed with toluene. The toluene used for washing and the filtrate are gathered and evaporated dry, obtaining 5.3 g (97% yield) of the desired product.

The product obtained has the following elementary analysis: C%=73.93 (theoretical 73.67); H%=9.60 (theoretical 9.05); P%=6.11 (theoretical 6.79); molecular weight $(MH)^+=1824$.

EXAMPLE 7

Preparation of
4,11,18,25-tetramethyl-1,8,15,22-tetrapentyl-[1₄]-metacyclophane-3-26,5-10,12-17,19-24, tetrakis(2,4-di-t-butylphenyl)phosphite (Compound N. 7)

With same method used in Example 1, are introduced in a 250 ml flask in order: 100 ml of toluene, 3 g (3.6 mmoles) of 4,11,18,25-tetramethyl-1,8,15,22-tetrapentyl- [1₄]-metacyclophane-3,26,5,10,12,17,19,24-octol, 4 ml of triethylamine and 4.42 g (3.6 mmoles) of 2,4-di-t-butyl-dichlorophosphite.

Operating as described for the Example 1,5.4 g (85% yield) of the desired product are isolated. The product obtained has the following elementary analysis: C%=72.7 (theoretical 73.27); H%=8.57 (theoretical 8.88); P%=6.85 (theoretical 7.00); molecular weight (MH)+ =1769.

EXAMPLE 8

Preparation of 4,11,18,25-tetramethyl-1,8,15,22-tetrapentyl-[1₄]-metacyclophane-3-26,5-10,12-17,19-24, tetrakis-(2,4,6-tri-t-butyl phenyl)phosphite (Compound N. 8)

With the same method used in Example 1, are introduced in a 250 ml flask in order: 100 ml of toluene, 3 g (3.6 mmoles) of 4,11,18,2 5-tetramethyl-1,8,15,2 2-tetrapentyl-[1₄]-metacyclophane-3,26,5,10,12,17,19,24-octol, 4 ml of triethylamine and 5.3 g (3.6 Moles) of 2,4,6-tri-t-butyl-dichlorophosphite. Operating as described for Example 1,5.9 g (83% yield) of the desired product are isolated. The product obtained has the following elementary analysis: C%=74.3 (theoretical 74.65); H%=9.37 (theoretical 9.50); P%=5.95 (theoretical 6.22); molecular weight (MH)+ =1993.

EXAMPLE 9-15 AND COMPARATIVE EXAMPLES 1-3

The following examples illustrate the efficiency of the phosphites which are the object of the present invention in combination with a phenolic antioxidant in the thermal stabilization of the polypropylene, and show the advantageous results derived from the use of said phosphites compared to the use of a phosphite and a phosphonite already known in the field of thermal stabilizers for polymers.

Into a 1 liter flask equipped with an agitator, 0.05 parts by weight of pentaerythrityl-tetrakis [3- (3,5-di-tert-butyl-4-hydroxyphenyl)propanoate], sold by Ciba Geigy under the Irganox 1010 trademark, and an appropriate quantity of one of the phosphites prepared according to Examples 1-6 are mixed as acetone solutions (100 ml) to 100 parts by weight of isotactic polypropylene in flakes form, having an isotactic index of about 96%, MFRL of 12 g/10 minutes.

The suspension is maintained under agitation for 1 hours, and the solvent is removed under vacuum at 50° C.

To the mixture thus obtained are added 0.1 parts by weight of calcium stearate, and the solids are blended in a mechanical mixer (3000 rpm) for about 10 minutes.

The resulting polymer compositions are extruded in a single screw extruder (screw velocity 45 rpm) operating at 230° C. The mixtures are extruded 5 times, and after each extrusion the MFR (Melt Flow Rate) is measured at 230° C. according to ASTM regulations, method 1238, condition L.

The amount and type of phosphite used, as well as the MFR measured after the first, third and fifth extrusion (respectively MFR$_1$, MFR$_3$, MFR$_5$), and the values of the MFR$_5$/MFR$_1$ ratio for each composition, are shown in Table 1.

EXAMPLE 16 AND COMPARATIVE EXAMPLE 4

In a 1 liter flask equipped with an agitator, 0.05 parts by weight of pentaerythrityl-tetrakis [3- (3,5-di-tert-butyl-4-hydroxyphenyl)propanoate], sold by Ciba Geigy under the Irganox 1010 trademark, and an appropriate quantity of one of the phosphites prepared according to Examples 1-6, are mixed as acetone solutions (100 ml) to 100 parts by weight of isotactic polypropylene in flakes form, having an isotactic index of about 96%, MFR of 12 g/10 minutes.

The suspension is maintained under agitation for 1 hour, and the solvent is removed under vacuum at 50° C.

To the mixture thus obtained are added 0.1 parts by weight of calcium sterate, and the solids are blended in a mechanical mixer (3000 rpm) for about 10 minutes.

The resulting polymer compositions are extruded in a single screw extruder (screw velocity 45 rpm) operating at 260° C. The mixtures are extruded 5 times, and measured at 230° C. according to ASTM regulations, method 1238, condition L.

The amount and type of phosphite used, as well as MFR measured after the first, third, and fifth extrusion (respectively MFR$_1$, MFR$_3$, MFR$_5$) are shown in Table 2.

Other features, advantages and embodiments of the invention disclosed herein will be readily apparent to those exercising ordinary skill after reading the foregoing disclosure.

In this regard, while specific embodiments of the invention have been described in considerable detail, variations and modifications of these embodiments can be effected without departing from the spirit and scope of the invention as described and claimed.

TABLE 1

| Example No. | Stabilizers | Concentr. Stabilizer (parts by weight) | MFR$_1$ | MFR$_3$ | MFR$_5$ | MFR$_5$/MFR$_1$ |
|---|---|---|---|---|---|---|
| 9 | Compound No. 1 | 0.05 | 10.7 | 11.8 | 16.0 | 1.5 |
| 10 | Compound No. 2 | 0.05 | 10.6 | 12.8 | 16.8 | 1.6 |
| 11 | Compound No. 3 | 0.05 | 10.7 | 13.0 | 16.4 | 1.5 |
| 12 | Compound No. 4 | 0.05 | 10.4 | 11.8 | 17.1 | 1.6 |
| 13 | Compound No. 5 | 0.10 | 10.6 | 11.5 | 12.9 | 1.2 |
| 14 | Compound No. 3 | 0.10 | 10.7 | 11.0 | 11.3 | 1.05 |
| 15 | Compound No. 6 | 0.10 | 10.6 | 11.5 | 12.3 | 1.2 |
| Compar. 1 | — | — | 12.4 | 19.6 | 25.8 | 2.1 |
| Compar. 2 | Sandostab P-EPQ[1] | 0.05 | 10.8 | 13.9 | 18.5 | 1.7 |

TABLE 1-continued

| Example No. | Stabilizers | Concentr. Stabilizer (parts by weight) | $MFR_1$ | $MFR_3$ | $MFR_5$ | $MFR_5/MFR_1$ |
|---|---|---|---|---|---|---|
| Compar. 3 | Irgafos 168[2] | 0.05 | 11.1 | 15.6 | 20.5 | 1.85 |

[1] Registered trademark of the product sold by Sandoz the main ingredient of which is: tetrakis(2,4-di-tert-butylphenyl)4,4'-diphenylilene diphosphonite.
[2] Registered trademark of the compound sold by CIBA-GEIGY of the formula: tris(2,4-di-tert-butylphenyl)-phosphite.

TABLE 2

| Example No. | Stabilizers | Concentr. Stabilizer (parts by weight) | $MFR_1$ | $MFR_3$ | $MFR_5$ |
|---|---|---|---|---|---|
| 16 | Compund. n. 7 | 0.1 | 2.2 | 2.6 | 3.5 |
| Compar. 4 | Sandostab P-EPQ | 0.1 | 2.2 | 2.8 | 3.5 |

We claim:

1. Polymer compositions comprising the phosphites of the formula:

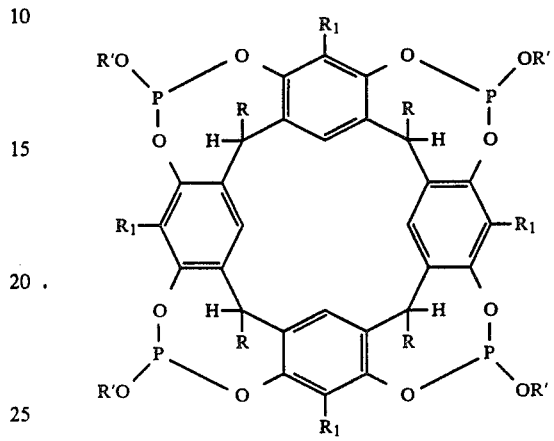

where R, equal or different, are H; linear or branched $C_1$-$C_{30}$ alkyl radicals; $C_5$-$C_6$ alicyclic radicals; $C_7$-$C_{12}$ aralkyl radicals; 2-furfuryl or phenyl radicals, optionally substituted by one or more electron donor groups selected from alkyl and alcoxyl groups, and present in the para or meta positions, or both; 2-cyclohexylethyl or p-phenylphenyl; R', equal or different, are $C_1$-$C_{30}$ alkyl radicals, or $C_5$-$C_{30}$ simple or condensed alicyclic radicals; aryl radicals, simple, double, or condensed, optionally substituted with $C_1$-$C_9$ alkyl groups, or with aryl groups joined by a heteroatom, or by a $C(R_2R_3)$ group, where $R_2$ and $R_3$, equal or different, are H, or $C_1$ - $C_5$ alkyl, or $C_6$-$C_{10}$ aryl radicals; $R_1$ radicals, equal or different, are H or $C_1$-$C_4$ alkyl radicals; with the proviso that when R is H, $R_1$ are $C_1$-$C_4$ alkyls.

2. Polymer compositions of claim 1 comprising from 0.01 to 3 parts by weight of phosphites per 100 parts by weight of polymer material.

3. Polymer compositions of claim 1, where the polymer material comprises one or more polymers or copolymers, or mixture thereof, obtained by way of sequential polymerization of olefins of formula R"CH=$CH_2$ where R" is a hydrogen atom, or a 1-6 carbon alkyl or aryl radical.

* * * * *

UNITED STATES PATENT AND TRADEMARK OFFICE
CERTIFICATE OF CORRECTION

PATENT NO.  : 5,326,801
DATED       : July 5, 1994
INVENTOR(S) : Marco Foa et al.

It is certified that error appears in the above-identified patent and that said Letters Patent is hereby corrected as shown below:

Col. 7, line 45, change "metacyclophane-3-6" to

--metacyclophane-3-26--

Col. 8, line 57, change "(24 Moles)" to --(24 mmoles)--

Signed and Sealed this

Eighteenth Day of July, 1995

Attest:

BRUCE LEHMAN

*Attesting Officer*  *Commissioner of Patents and Trademarks*